(12) United States Patent
Hodorek et al.

(10) Patent No.: US 11,850,157 B2
(45) Date of Patent: *Dec. 26, 2023

(54) RADIAL HEAD ORTHOPEDIC IMPLANT APPARATUS AND METHOD OF USING SAME

(71) Applicant: Synthes GmbH, Oberdorf (CH)

(72) Inventors: Brian C. Hodorek, Winona Lake, IN (US); Matt J. Purdy, Winona Lake, IN (US); J. Michael Wiater, Beverly Hills, MI (US); Anand M. Murthi, Baltimore, MD (US); Matthew J. Smith, Columbia, MO (US); Derek J. Cuff, Venice, FL (US); Andrew Jawa, Cambridge, MA (US)

(73) Assignee: Synthes GmbH

(*) Notice: Subject to any disclaimer, the term of this patent is extended or adjusted under 35 U.S.C. 154(b) by 170 days.

This patent is subject to a terminal disclaimer.

(21) Appl. No.: 17/313,050

(22) Filed: May 6, 2021

(65) Prior Publication Data

US 2021/0275312 A1 Sep. 9, 2021

Related U.S. Application Data

(63) Continuation of application No. 16/025,940, filed on Jul. 2, 2018, now Pat. No. 11,020,234.

(60) Provisional application No. 62/632,987, filed on Feb. 20, 2018.

(51) Int. Cl.
*A61F 2/38* (2006.01)
*A61F 2/30* (2006.01)

(52) U.S. Cl.
CPC .. *A61F 2/3804* (2013.01); *A61F 2002/30224* (2013.01); *A61F 2002/30593* (2013.01); *A61F 2002/3827* (2013.01)

(58) Field of Classification Search
CPC .......... A61F 2/3804; A61F 2002/30224; A61F 2002/30593; A61F 2002/3827
See application file for complete search history.

(56) References Cited

U.S. PATENT DOCUMENTS

| | | |
|---|---|---|
| 6,656,225 B2 | 12/2003 | Martin |
| 7,160,329 B2 | 1/2007 | Cooney et al. |
| 7,637,908 B1 | 12/2009 | Gonzalez-Hernandez |
| 7,641,695 B2 | 1/2010 | Guederian |
| 8,100,980 B2 | 1/2012 | Ikegami et al. |
| 8,366,781 B2 | 2/2013 | Berelsman et al. |
| 8,425,615 B2 | 4/2013 | Berelsman et al. |

(Continued)

OTHER PUBLICATIONS

US 9,668,869 B2, 06/2017, Katrana et al. (withdrawn)

*Primary Examiner* — Keri J Nelson
*Assistant Examiner* — Rebecca Lynee Zimmerman
(74) *Attorney, Agent, or Firm* — BakerHostetler

(57) ABSTRACT

An orthopedic implant apparatus, said apparatus comprising: a body, said body having a generally cylindrical shape and comprising a first material, a flat bottom surface, a concave upper surface disposed opposite said bottom surface, and a longitudinal axis disposed through the center of said body; a cylindrical bore, said bore disposed along said longitudinal axis through said top surface of said body; cylindrical plug, said plug comprising a second material and disposed within said bore of said body; and at least one stem, said at least one stem connected to said bottom surface of said body.

19 Claims, 16 Drawing Sheets

(56) References Cited

U.S. PATENT DOCUMENTS

| | | |
|---|---|---|
| 8,535,382 B2 | 9/2013 | Kehres et al. |
| 8,920,509 B2 | 12/2014 | Katrana et al. |
| 9,034,050 B2 | 5/2015 | Katrana et al. |
| 9,039,779 B2 | 5/2015 | Winslow |
| 9,561,110 B2 | 2/2017 | Graham et al. |
| 9,636,228 B2 | 5/2017 | Leibel |
| 9,655,726 B2 | 5/2017 | Cooney et al. |
| 9,763,792 B2 | 9/2017 | Bergquist et al. |
| 2006/0100715 A1* | 5/2006 | De Villiers ............ A61F 2/4241 623/23.4 |
| 2014/0074246 A1* | 3/2014 | Huebner ................ A61F 2/3804 623/20.11 |
| 2016/0235543 A1 | 8/2016 | Hwa |
| 2018/0280150 A1 | 10/2018 | Kartholl et al. |

* cited by examiner

RADIAL HEAD ORTHOPEDIC IMPLANT APPARATUS AND METHOD OF USING SAME

CROSS-REFERENCE TO RELATED APPLICATIONS

This is a continuation of U.S. patent application Ser. No. 16/025,940 filed Jul. 2, 2018, which claims the benefit of U.S. patent application Ser. No. 62/632,987 filed Feb. 20, 2018.

BACKGROUND

1. Field of the Invention

The present invention relates generally to the field of orthopedic implants. More particularly, the present invention relates to orthopedic radial head implants.

2. Description of the Related Art

Trauma to the elbow joint frequently involves damage to the ligamentous support of the elbow and fractures of the osseous structures responsible for the skeletal integrity of the elbow joint. The proximal aspect of the radius, or radial head, is frequently injured either in isolation or in combination with injury to other bony or ligamentous structures of the elbow joint. The radial head may also be fractured in association with injuries to the forearm axis, including disruptions of the interosseous membrane between the radius and the ulna. Whether in isolation or in combination with other injuries, fractures of the radial head can be difficult to treat.

Fractures of the radial head are either reconstructable or unreconstructable. Despite various technical advances in the reconstruction of radial head fractures, a certain percentage of fractures are not amenable to reconstruction due to the degree comminution or severity of the fracture. In general, unreconstructable radial head fractures result from high energy trauma and are therefore frequently associated with significant injuries to other osseous or ligamentous structures of the elbow joint or forearm. In these cases, restoration of the stabilizing function of the radial head is critical to allow the ligaments of the elbow or forearm to heal in appropriate relationships, thereby restoring stability to the elbow or forearm. This stabilizing function depends, in part, upon re-establishing the appropriate distance between the capitellum and the proximal shaft of the radius.

The first widely used prosthetic radial head was introduced in the 1970's and was composed of silicone. Silicone implants placed in various joints throughout the body led to "silicon synovitis," in which the silicone induces an inflammatory response within the joint. Further, silicone radial head prostheses were found to be incapable of resisting the stresses to which the radial head is subjected, rendering it less useful in stabilizing the injured elbow or forearm.

The difficulties apparent with silicone led to experimentation with metal radial head implants. These prostheses may be fashioned from a single piece of metal or multiple pieces of metal (often titanium) and include a stem and a head portion. Most systems have an articular surface (head) made of cobalt chrome and a stem made of titanium or cobalt chrome. However, a device may also comprise stainless steel.

The head portion is shaped to approximate the anatomy of the radial head. These metallic prostheses are capable of resisting the compressive stresses to which the radial head is subjected, as has been demonstrated in several biomechanical studies. However, significant problems remain with these prostheses.

Anatomic and radiographic studies of the dimensions of the radial head reveal a disparity with currently available metallic prostheses. Therefore, it has been difficult to restore appropriate anatomic alignments within the elbow. Therefore, restoration of the appropriate relationship between the capitellum and proximal shaft of the radius has been very difficult to achieve with these prostheses.

Thus, a need exists for new radial head implant devices. Exemplary prior art devices are shown below.

U.S. Pat. No. 9,763,792 discloses a system for replacing an end of a bone, such as a radial bone, with a prosthesis. In exemplary embodiments, the prosthesis is a radial head prosthesis having a stem portion and a head portion. The head portion may be configured to be (a) placed onto the stem portion by movement of the head and stem portions relative to one another transverse to a longitudinal axis of the stem portion, and then (b) rotated with respect to the stem portion to produce friction that firmly attaches the head portion to the stem portion.

U.S. Pat. No. 9,668,869 discloses an elbow prosthesis including a stem structure and an articulating component. The stem structure is operable to be positioned in a bone of a joint and includes a stem portion and a C-shaped body portion. The stem portion is operable to be positioned in the bone. The C-shaped body portion includes a first articulating surface bound by a medial wall and a lateral wall. The medial and lateral walls are separated by a first distance. The articulating component includes a second articulating surface positioned between a medial side surface and a lateral side surface. The medial and lateral side surfaces are separated by a second distance that is less than the first distance. The second articulating surface is configured to slidably communicate in a medial/lateral direction along the first articulating surface of the C-shaped body portion.

U.S. Pat. No. 9,655,726 discloses a radial-capitellar implant for surgical replacement of the capitellum of the humerus and, optionally, the head of the radius. The radial-capitellar implant includes a capitellar implant or surface replacement arthroplasty of the capitellum and a radial prosthesis for replacement of the head of the radius. In one embodiment the radial prosthesis includes an articular head which moveable articulates with a stem implantable in the radius.

U.S. Pat. No. 963,228 discloses a radial head implant including a head, a stem, and a locking mechanism, whereby the head laterally engages the stem, and an instrument for implanting and removing such implant is described.

U.S. Pat. No. 9,561,110 discloses an elbow prosthesis including a capitellar implant having an articulating head and a stem. The articulating head can have a first articulating surface positioned generally between a lateral side and a medial side. A passage can extend through the articulating head from the lateral side to the medial side. The articulating head can define a counterbore formed at the lateral side and that is concentric with the passage. According to other features, the elbow prosthesis can include a coronoid implant that has a body and a stem. The body can have a superior articulating surface that includes a central ridge and an anterior buttress. The central ridge can be configured to accommodate articulation with a trochlea in an implanted position.

U.S. Pat. No. 9,039,779 discloses an elbow prosthesis having a first stem component attached to one of a humerus and an ulna, a second stem component attached to the other of the humerus and the ulna, and a joint disposed between and coupling the first stem component and the second stem component to permit relative movement between the first stem component and the second stem component about a first axis. The elbow prosthesis may additionally include a condyle extending from the joint and including an axis of rotation that is eccentric from the first axis.

U.S. Pat. No. 9,034,050 discloses an elbow prosthesis including a capitellar implant that has an articulating head and a stem. The articulating bead can have a first substantially hemispherical portion and a second portion that collectively extend between lateral and medial sides of the articulating head and are separated by a plane. The first and second portions can generally extend between the lateral and medial sides. The second portion can generally have an attachment lobe that extends on the lateral side and that defines a passage therethrough. The passage can extend at least partially on the second portion.

U.S. Pat. No. 8,920,509 discloses a prosthesis system for replacement of a head portion of a proximal radius can include an articulation component having a first connection portion. A first head component can have a second connection portion that connects to the first connection portion. A second head component can have a third connection portion that connects to the first connection portion. The second head component can have a distinct dimension from the first head component. A stem component can include a fourth connection portion that connects with either of the first or second head components. The stem component can have a stem anchoring portion that connects to the radius.

U.S. Pat. No. 8,535,382 discloses a prosthesis system for replacement of a head portion of a proximal radius. The system can include a first polymeric articulation component having a first locking portion and a metal head component having a second locking portion. The second locking portion can mate with the first locking portion to form a first locking mechanism to initially couple the first articulation component to the head component. The head component can define a locking channel. The system can also include a stem component having a protrusion receivable in the locking channel. The protrusion can define a bore, and the stem component can be adapted to be coupled to the radius. The system can also include a fastener received through the locking channel and into the bore to provide a second locking mechanism that couples the head component to the stem component.

U.S. Pat. No. 8,425,615 discloses a modular prosthesis system for replacement of a head portion of radius. The prosthesis system includes a head component having a first connection portion that connects to a second connection portion and a collar component having the second connection portion and a third connection portion. The system also includes a stem component including a fourth connection portion that connects with the third connection portion, the stem component having a stem anchoring portion that connects to the radius. The collar component provides the modular geometry to the prosthesis without having to have an increased number of head components and stem components with variable lengths and angles.

U.S. Pat. No. 8,366,781 discloses a modular prosthesis system for replacement of a head portion of a proximal radius includes a monolithic stem component, a head component, and a locking mechanism formed by the stem and head components. The stem component defines a stem anchoring portion having a longitudinal axis and configured to couple to the proximal radius, and a dovetail-shaped first mourning portion on a first end face that extends in a first direction transverse to the longitudinal axis. The head component has a dovetail-shaped second mounting portion on a second end face opposite the first end face slidably engaged with the first mounting portion along the first direction. One of the first and second mounting portions intersects the longitudinal axis. The locking mechanism is formed at an interface between the stem and head components and is engaged through relative translational movement between the stem and head components. A related method is provided.

U.S. Pat. No. 8,100,980 discloses an artificial elbow joint including a humeral component made of metal and an ulnar component made of resins for replacing an elbow joint. The humeral component of this artificial elbow joint is configured by a substantially cylindrical trochlea and a stem extending from the trochlea that is inserted into the humeral; and the ulnar component is configured by a joint surface member which receives the trochlea of humeral component in a rotatable manner and a stem which extends from the joint surface member and is inserted into the ulna. The stem of the humeral component is curved gently downward overall so as to comply with the lordotic shape of the humeral, and the trochlea is turnable about the centerline of the stem.

U.S. Pat. No. 7,641,695 discloses a modular endoprosthetic radial head implant includes an end cap secured to a cannulated body held to bone by a fixation element. The fixation element supports the cannulated body on a resected radial bone end, for example. The fixation element of one embodiment features a threaded stem with a spherical head. The stem fits distally into the cannulated body and extends through a hole formed by the distal end of the cannulated body. The spherical head nests inside the cannulated body. Polyaxial alignment between the cannulated body and the fixation element is locked using a jam nut tightened inside the cannulated body. An end cap fits into place proximally on the cannulated body. The end cap is formed of a joint surface material to provide a bearing surface.

U.S. Pat. No. 7,637,908 discloses a system for intramedullary subchondral support fixation of radial head fractures is disclosed. An illustrative embodiment of the system includes an insertion plate having a head segment, a neck segment extending from the head segment, at least one shaft segment extending from the neck segment and at least one tail segment extending from the at least one shaft segment. A plurality of fastener openings may be provided in the insertion plate and a plurality of fasteners may extend through at least two of the plurality of fastener openings, respectively. A method for intramedullary subchondral support fixation of radial head fractures is also disclosed.

U.S. Pat. No. 7,160,329 discloses a radial-capitellar implant for surgical replacement of the capitellum of the humerus and, optionally, the head of the radius. The radial-capitellar implant includes a capitellar implant or surface replacement arthroplasty of the capitellum and a radial prosthesis for replacement of the bead of the radius. In one embodiment the radial prosthesis includes an articular head which moveable articulates with a stem implantable in the radius.

U.S. Pat. No. 6,656,225 discloses a modular prostheses system for replacement of the radial head portion of the radius bone, and methods for its use are disclosed. The system comprises a stem component comprising an anchoring portion and a mounting portion, and a head component having an open channel wherein the open channel is configured to connect to the mounting portion along an assembly axis that is transverse to a longitudinal axis of the stem component.

What is needed in the art is a modular radial implant that provides the flexibility to prevent damage to the capitellum while maintaining the strength of the fully metal device.

SUMMARY

In one exemplary embodiment, the present invention includes an orthopedic implant apparatus, said apparatus comprising: a body, said body having a generally cylindrical shape and comprising a first material, a flat bottom surface, a concave upper surface disposed opposite said bottom surface, and a longitudinal axis disposed through the center of said body; a cylindrical bore, said bore disposed along said longitudinal axis through said top surface of said body; a cylindrical plug, said plug comprising a second material and disposed within said bore of said body; and at least one stem, said at least one stem connected to said bottom surface of said body.

In another exemplary embodiment, the present invention includes an orthopedic implant apparatus, said apparatus comprising: a body, said body having a generally cylindrical shape, a flat bottom surface, a top surface disposed opposite said bottom surface, and a longitudinal axis disposed through the center of said body; an annular insert, said insert having a concave surface and a cylindrical bore disposed through the center of said insert, said insert disposed on said top surface of said body, said insert comprising a first material; a cylindrical plug, said plug disposed within said bore of said insert, said insert comprising a second material; and at least one stem, said at least one stem connected to said bottom surface of said body.

In another exemplary embodiment, the present invention includes an orthopedic implant apparatus, said apparatus comprising: a body, said body having a generally cylindrical shape and comprising: a first material, a flat bottom surface, a concave upper surface disposed opposite said bottom surface, and a longitudinal axis disposed through the center of said body; a plurality of plugs, each of said plugs comprising a hemispherical shape, said plugs disposed on top of and connected to said concave upper surface of said body; and at least one stem, said at least one stem connected to said bottom surface of said body.

BRIEF DESCRIPTION OF THE DRAWINGS

The present invention will be understood mere fully from the detailed description given hereinafter and from the accompanying drawings of the preferred embodiment of the present invention, which, however, should not be taken to limit the invention, but are for explanation and understanding only.

In the drawings.

Corresponding reference characters indicate corresponding parts throughout the several views. The exemplary embodiments set forth herein are not to be construed as limiting the scope of the invention in any manner.

DETAILED DESCRIPTION OF THE EMBODIMENTS

Figure 1:
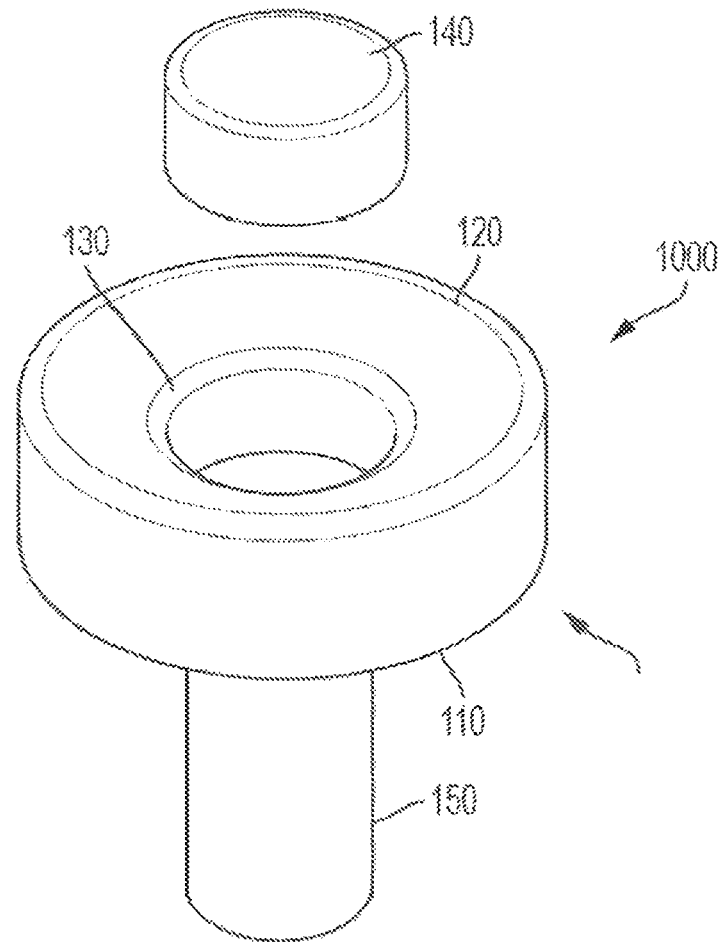
FIG. 1 shows an exploded perspective view of an apparatus in accordance with a first exemplary embodiment of the present invention.
Figure 2:
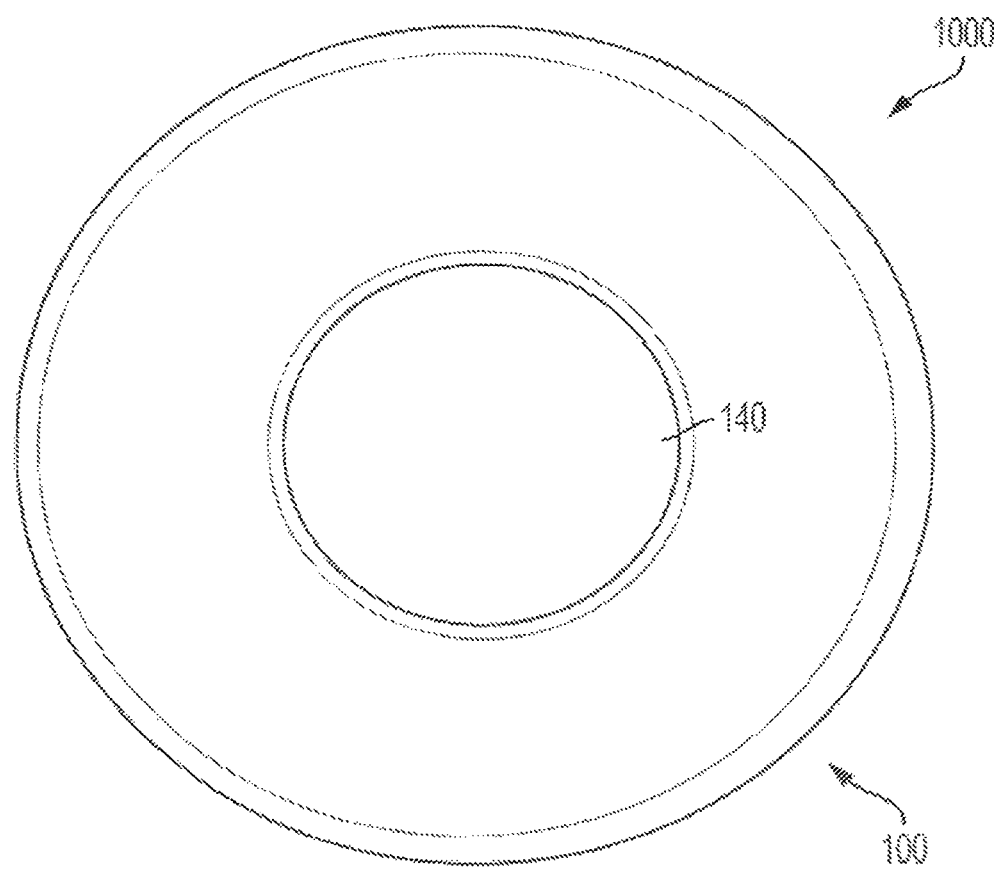
FIG. 2 shows a top view of an apparatus in accordance with a first exemplary embodiment of the present invention.
Figure 3:
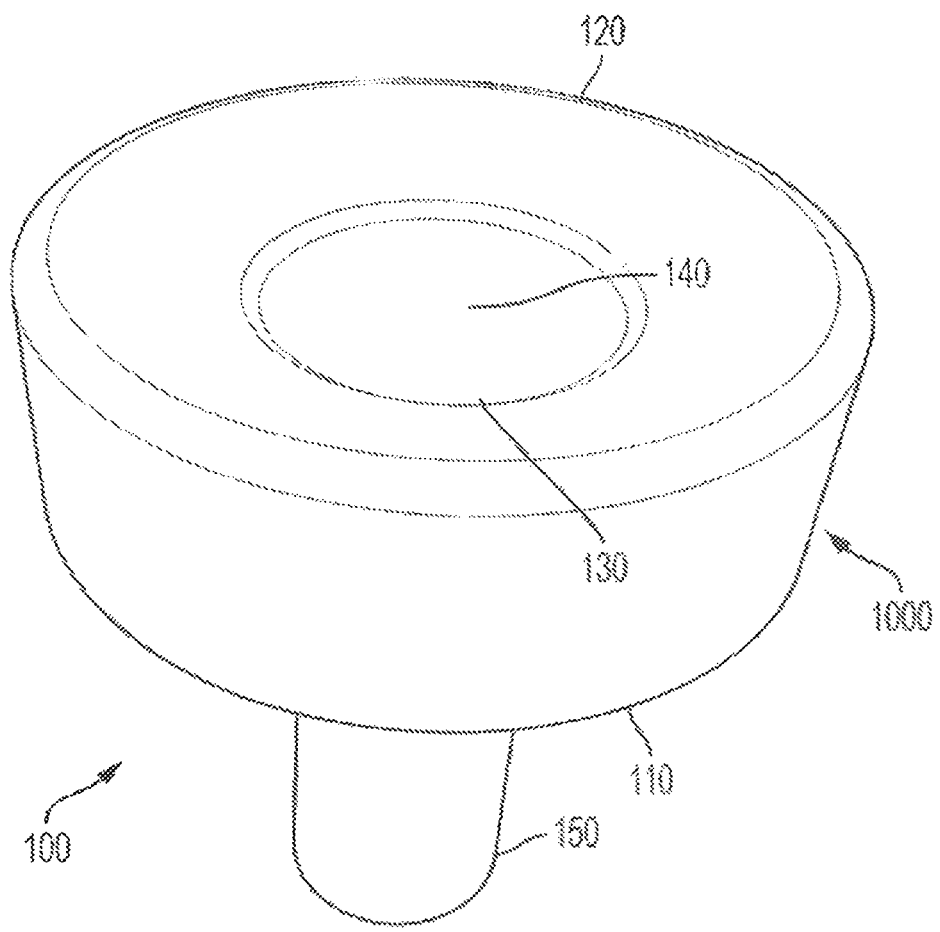
FIG. 3 shows a side perspective view of an apparatus in accordance with a first exemplary embodiment of the present Invention.
Figure 4:
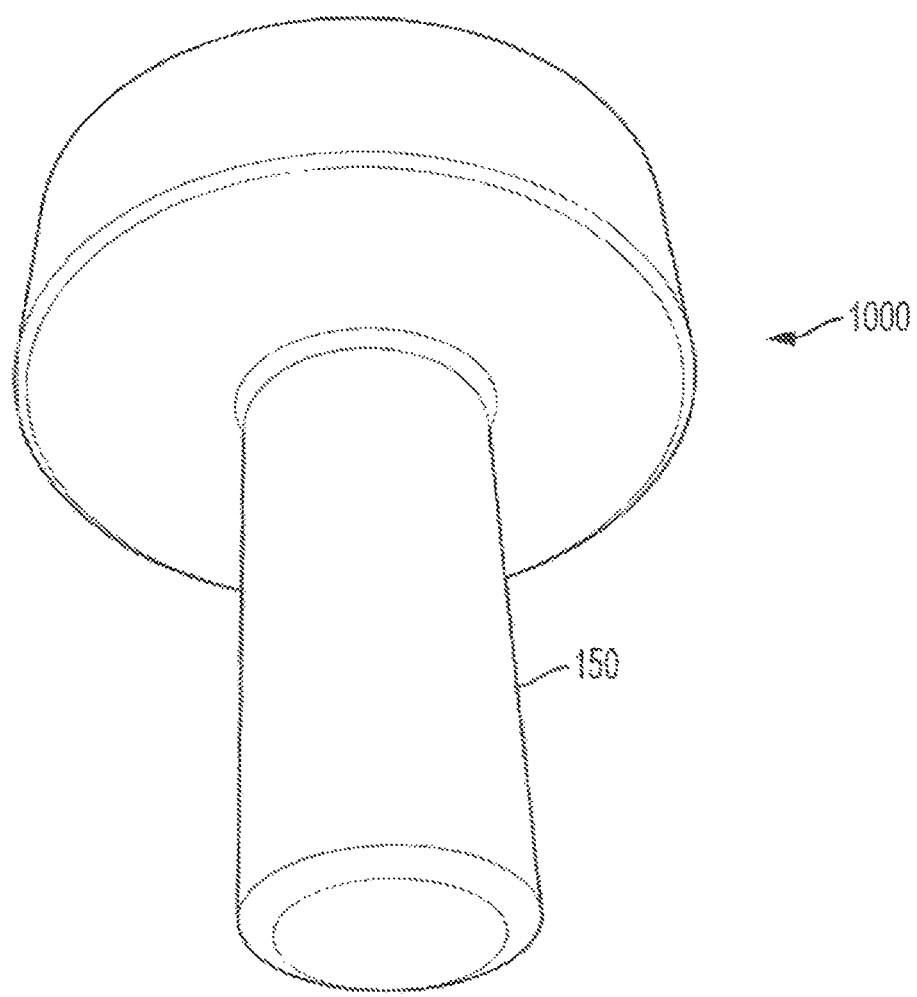
FIG. 4 shows a bottom perspective view of an apparatus in accordance with a first exemplary embodiment of the present invention.

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail to avoid unnecessary obscuring of the present invention.

Thus, all the implementations described below are exemplary implementations provided to enable persons skilled in the art to make or use the embodiments of the disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in FIG. 1.

Furthermore, there is no intention to be bound by any expressed or implied theory presented in the preceding Technical Field, Background, Summary or the following detailed description. It is also to be understood that the specific devices and processes illustrated in the attached drawings, and described in the specification, are simply exemplary embodiments of the inventive concepts defined in the appended claims. Hence, specific dimensions and other physical characteristics relating to the embodiments disclosed herein are not to he considered as limiting, unless the claims expressly state otherwise.

While there are many acceptable exposure methods, the Kaplan interval in a line from the lateral epicondyle toward Lister's tubercle, with the forearm in neutral rotation, permits the collateral ligament to be left intact. In fracture dislocations, the exposure is through the traumatic opening in the ligament complex. Proximally, the ECRL origin is released with the anterior capsule to permit direct access to the front of the radial head.

Thus, the surgical technique for implanting a radial head device generally comprises templating the radial head prior to surgery to determine the appropriate level of resection; resecting the radial head with a surgical saw as close to the surgical neck as possible; preparing the canal for the stem using sequentially larger broaches; reaming the radial canal prepare the same for the implant; planting the neck of the radius to ensure a flat surface perpendicular to the canal for the head of the implant; inserting the trail implant into the radius to evaluate the stem size, head diameter and head height; and replacing the trial implant with the final implant.

Referring generally to FIGS. 1-4, in one exemplary embodiment, radial orthopedic implant apparatus 1000 generally comprises a body 100. Body 100 is comprised of a biocompatible metal such as cobalt chrome, stainless steel, or titanium.

Referring still to FIGS. 1-4, body 100 of apparatus 1000 has a generally cylindrical shape and a flat bottom surface 110. Body 100 further comprises a concave upper surface 120 disposed opposite said bottom surface 110.

Referring again to FIGS. 1-4, body 100 further comprises a longitudinal axis (not shown) disposed through the center of body 100. Body 100 further comprises a cylindrical bore 130. Bore 130 is disposed along said longitudinal axis through said top surface 120 of body 100.

Referring again to FIGS. 1-4, apparatus 1000 further comprises a cylindrical plug 140. Cylindrical plug 140 comprises a second material distinct from the material of body 100 such as a biocompatible plastic polymer or thermoset polymer. Plug 140 may comprise polyethylene, ultra-high molecular weight polyethylene, cross-linked polyethylene, PEEK, hydrogel, ceramic, or any other non-metal material having mechanical properties suitable for a bearing component Referring still to FIGS. 1-4, body 100 of apparatus 1000 further comprises at least one stem 150. Stem 150 extends from bottom surface 110 of body 100 in a direction opposite top surface 120 of body 100. Stem 150 may comprise a smooth surface for movement within the radius or a porous surface or bone growth promoting material for fixation within the bone. It is further contemplated that a plurality of stems 150 may be provided to attach body 100 to a human radius. In alternative embodiments, other known means may be used to attach body 100 to a bone.

Figure 5:
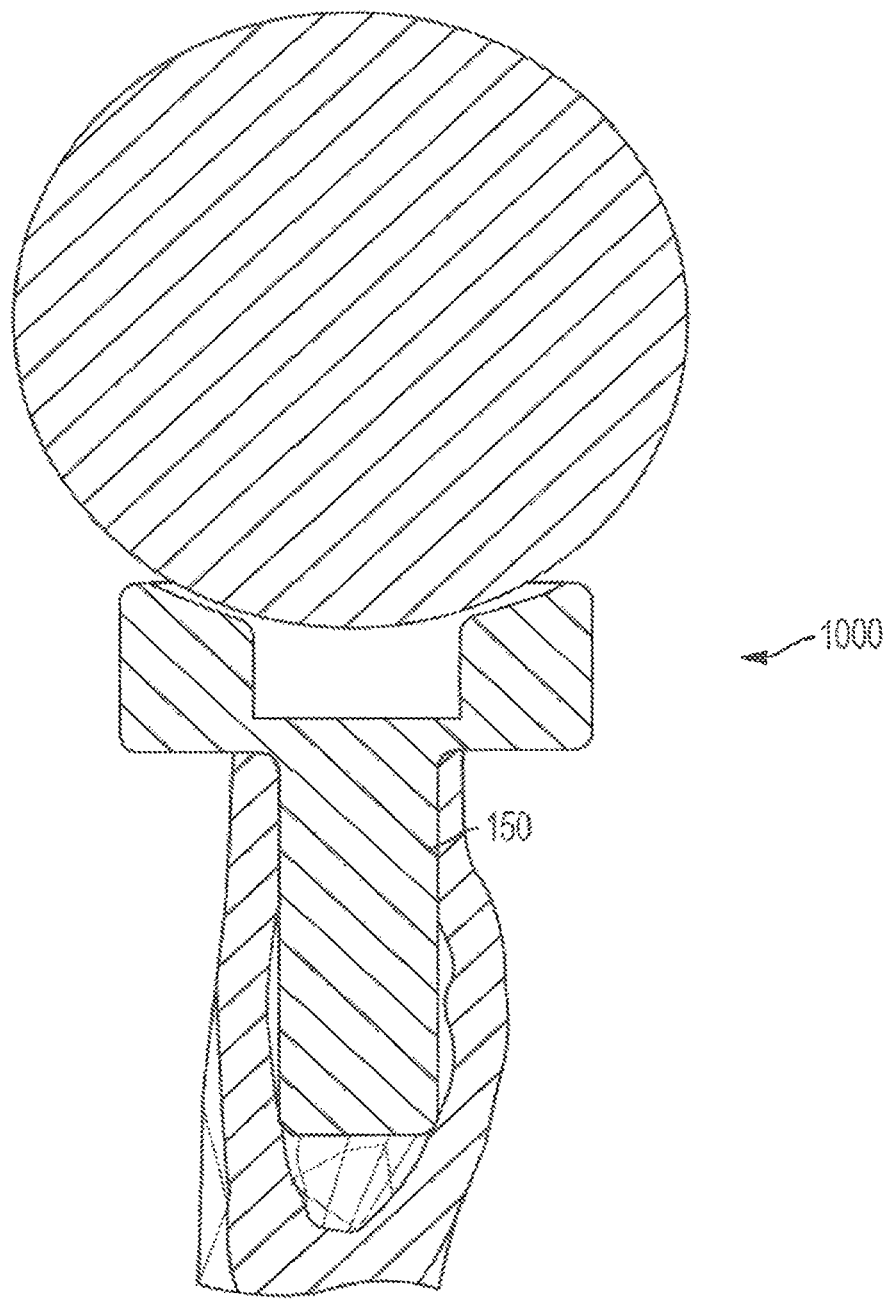
FIG. 5 shows a side view of an apparatus in accordance with a first exemplary embodiment of the present invention inserted into a radius bone.
Figure 6:
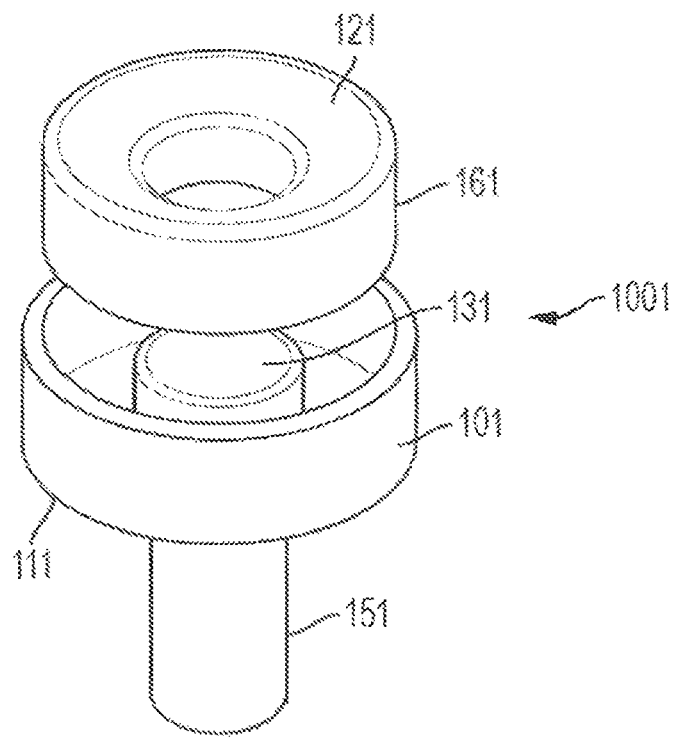
FIG. 6 shows an exploded perspective view of an apparatus in accordance with a second exemplary embodiment of the present invention.

Referring now to FIG. 5, there is shown a side view of apparatus 1000 in accordance with an exemplary embodiment of the present invention. As illustrated FIG. 5, apparatus 1000 is inserted into the intramedullary canal of a radial bone.

Referring generally to FIGS. 6-9, in another exemplary embodiment, radial orthopedic implant apparatus 1001 generally comprises a body 101. Body 101 is comprised of a biocompatible metal such as cobalt chrome, stainless steel, or titanium.

Referring still to FIGS. 6-9, body 101 of apparatus 1001 has a generally cylindrical shape and a flat bottom surface 111. Body 101 further comprises a concave upper surface 121 disposed opposite said bottom surface 111.

Referring again to FIGS. 6-9, body 101 further comprises a longitudinal axis (not shown) disposed through the center of body 101. Body 101 further comprises a cylindrical peg 131. Peg 131 is disposed along said longitudinal axis through said top surface 121 of body 101. Peg 131 extends from body 101 in the direction of upper surface 121 and comprises the same material as body 101.

Figure 7:
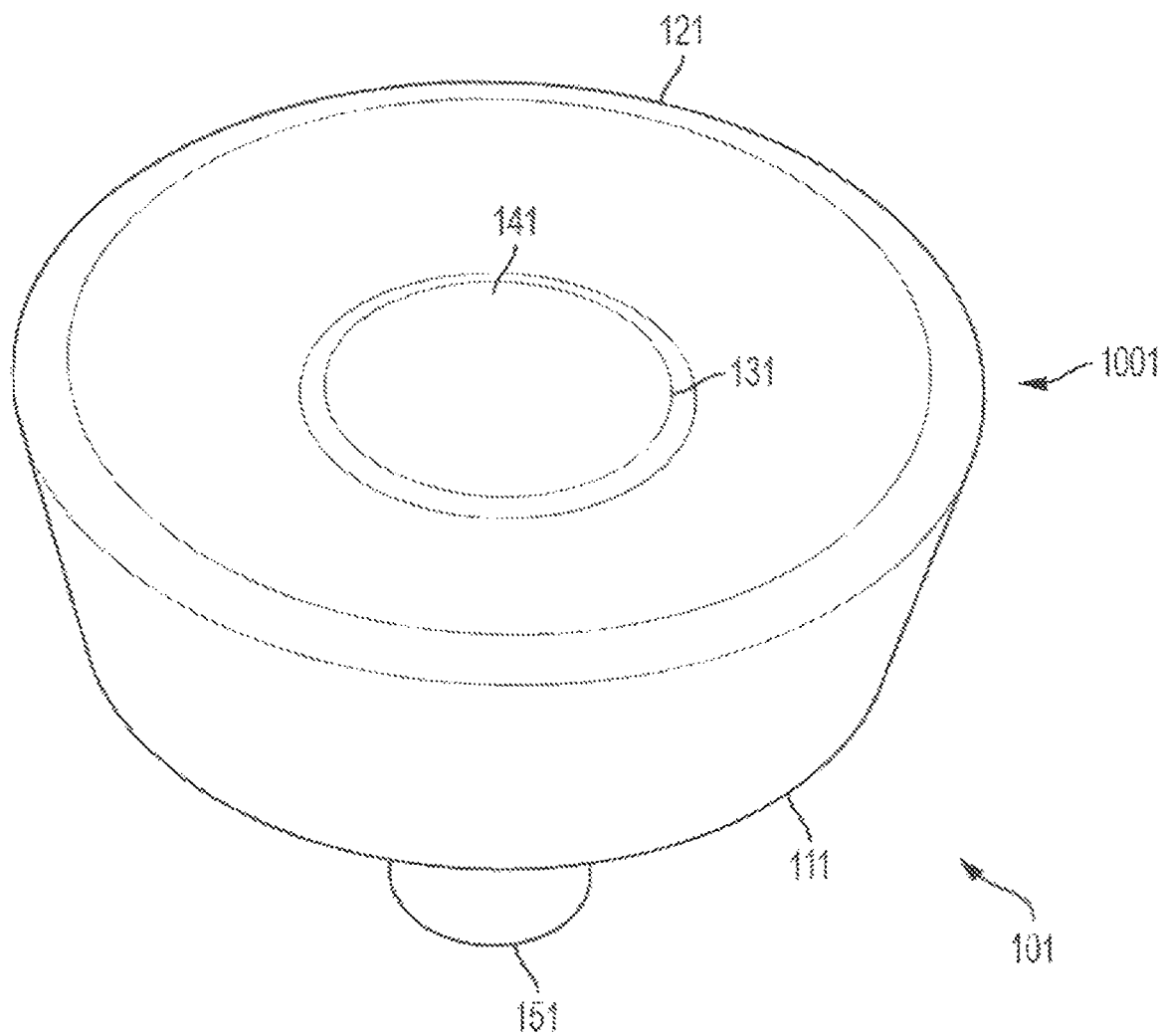
FIG. 7 shows a top perspective view of an apparatus in accordance with a second exemplary embodiment of the present invention.
Figure 8:
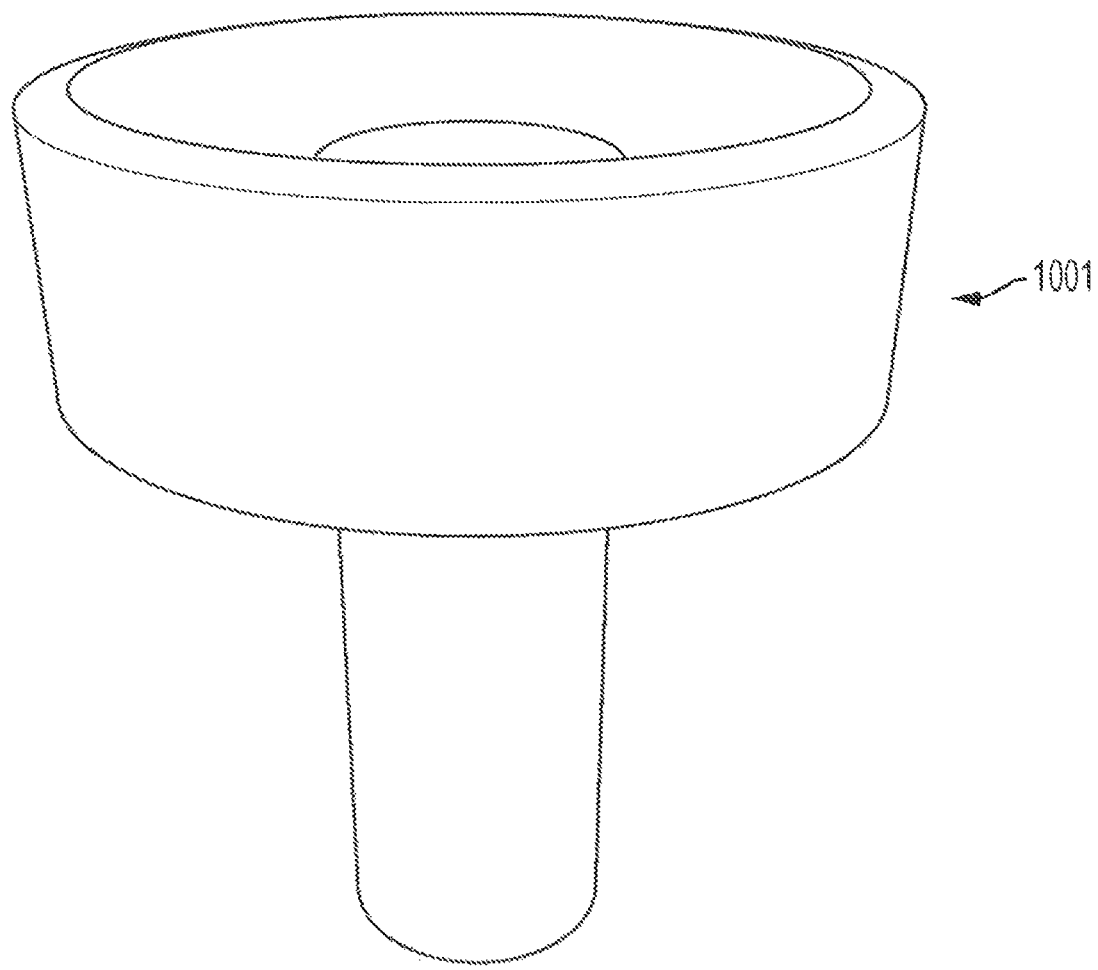
FIG. 8 shows a side perspective view of an apparatus in accordance with a second exemplary embodiment of the present invention.
Figure 9:
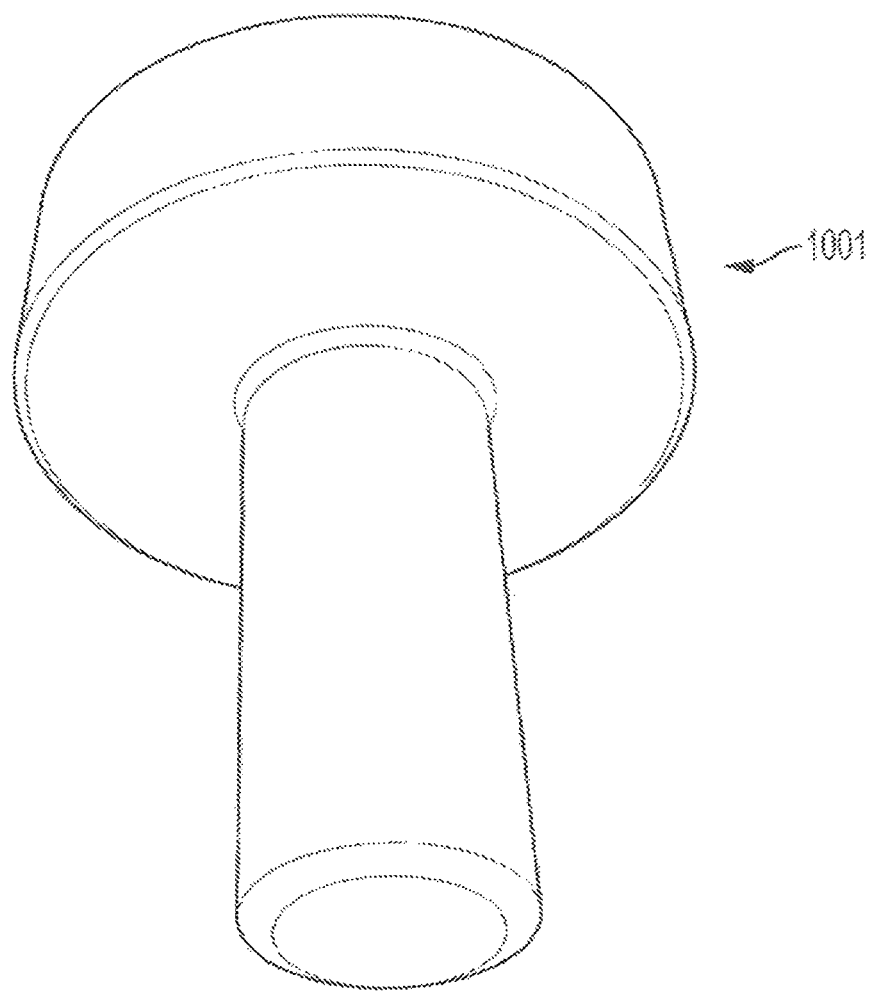
FIG. 9 shows a bottom perspective view of an apparatus in accordance with a second exemplary embodiment of the present invention.

Referring again to FIGS. 6-9, body 101 of apparatus 1001 further comprises a cylindrical ring 161. Cylindrical ring 161 comprises a second material distinct from the material of body 101 such as a biocompatible plastic polymer or thermoset polymer. Ring 161 may comprise polyethylene, ultra-high molecular weight polyethylene, cross-linked polyethylene, PEEK, hydrogel, ceramic, or any other non-metal material having mechanical properties suitable for a bearing component. As illustrated in FIGS. 7-9, ring 161 is disposed on the top surface 121 of body 101 and peg 131 is disposed through the center of ring 161. Ring 161 further comprises a generally concave upper surface as illustrated in FIGS. 6-9.

Referring still to FIGS. 6-9, body 101 of apparatus 1001 further comprises at least one stem 151. Stem 151 extends from bottom surface 110 of body 101 in a direction opposite top surface 121 of body 101. Stem 151 may comprise a smooth surface for movement within the radius or a porous surface or bone growth promoting material for fixation within the bone. It is further contemplated that a plurality of stems 151 may be provided to attach body 101 to a human radius. In alternative embodiments, other known means may be used to attach body 101 to a bone.

Figure 10:
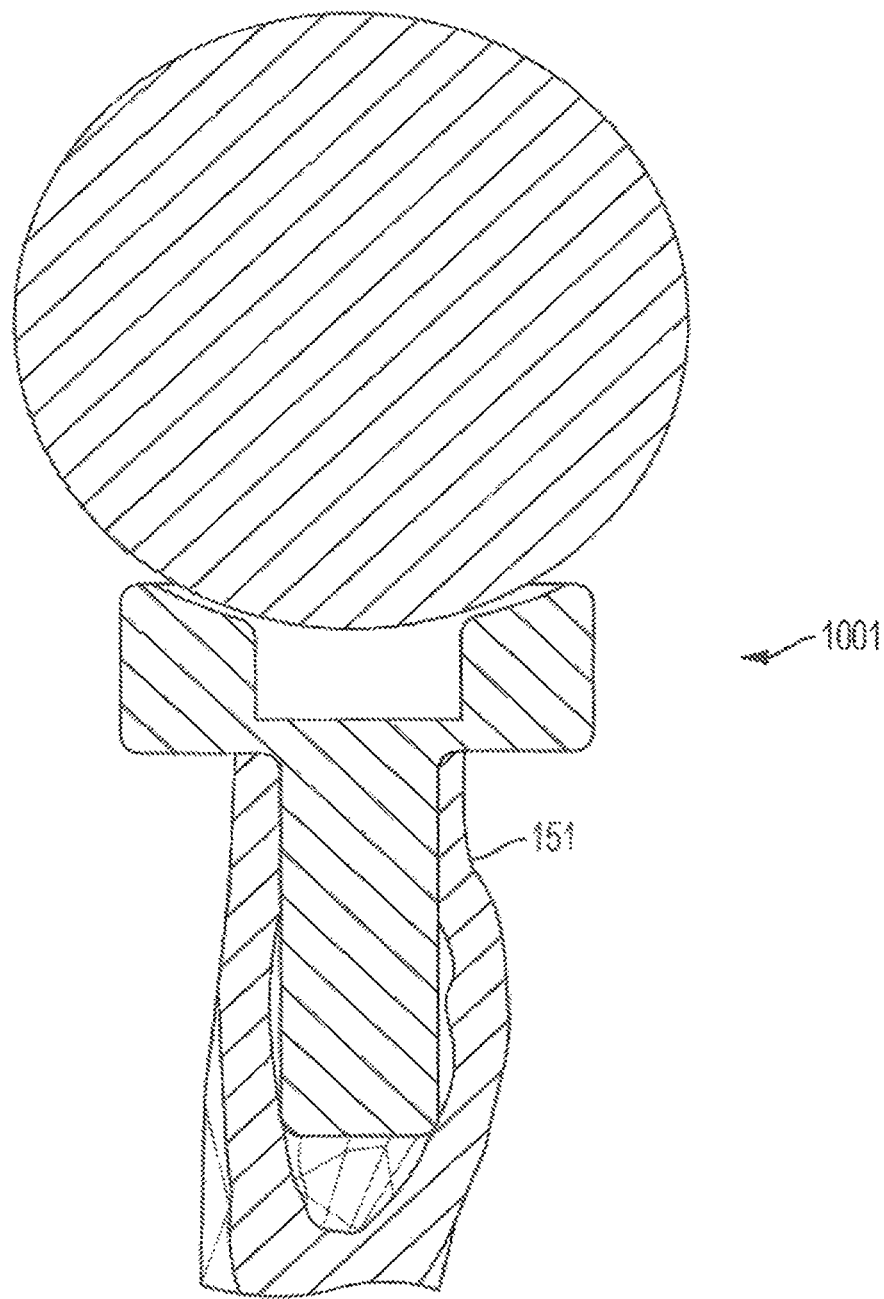
FIG. 10 shows a side view of an apparatus in accordance with a second exemplary embodiment of the present invention inserted into a radius bone.

Referring now to FIG. 10, there is shown a side view of apparatus 1001 in accordance with an exemplary embodiment of the present invention. As illustrated in FIG. 10, apparatus 1001 is inserted into the intramedullary canal of a radial bone.

Figure 11:
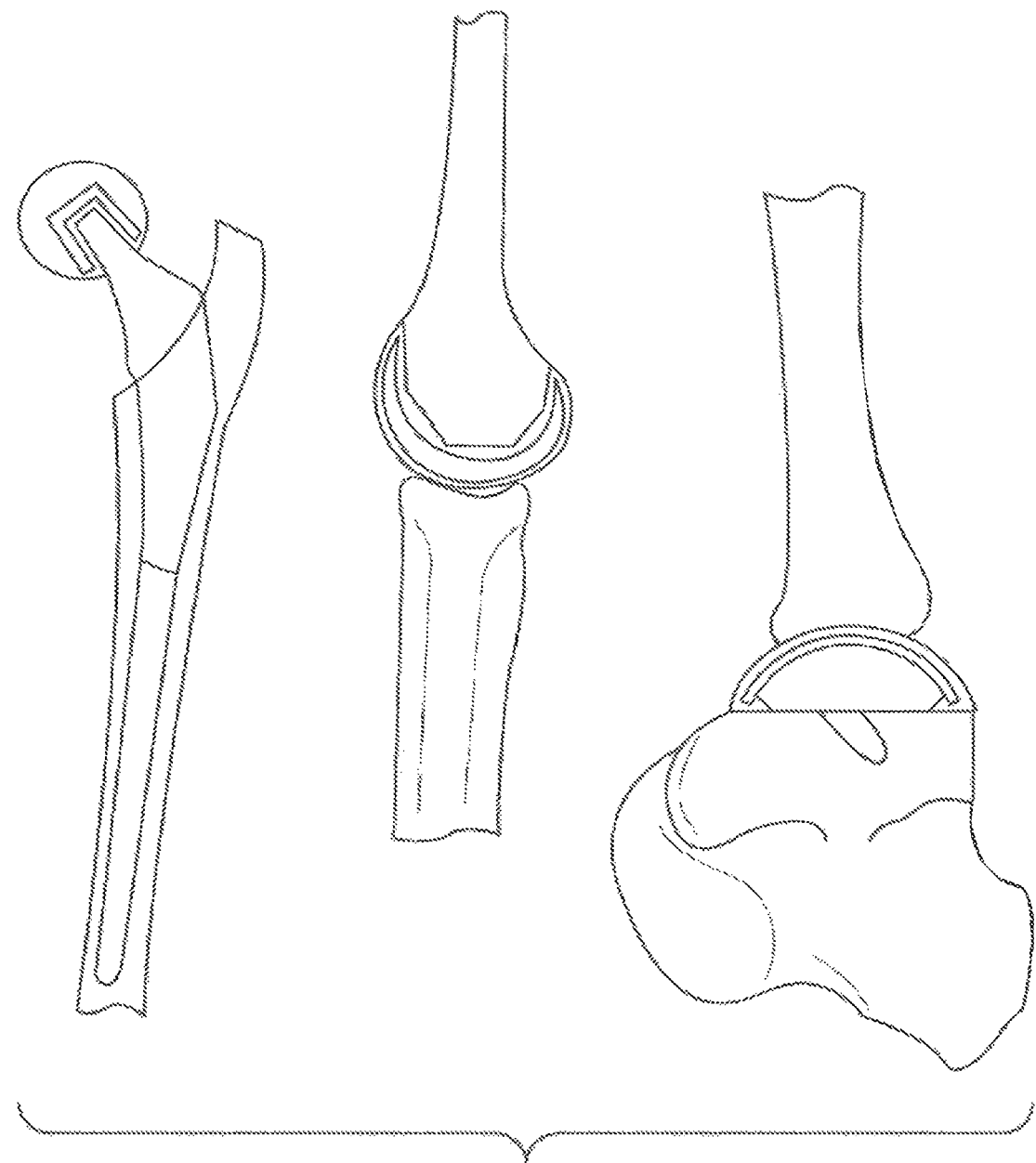
FIG. 11 shows an illustration of a difference between the second embodiment and the prior art.

Referring to FIG. 11, advantageously, because ring 161 is conical rather than spherical, the capitellum will not initially reside in or touch the central metal until, through plastic material conformity, the capitellum may touch the central metal portion and "load sharing" would result. Alternatively, although not shown, ring 161 may be spherical if the radius is large enough to achieve the same result.

Referring next generally to FUGS. 12-15, in another exemplary embodiment, radial orthopedic implant apparatus 1002 generally comprises a body 102. Body 102 is comprised of a biocompatible metal such as cobalt chrome, stainless steel, or titanium.

Figure 12:
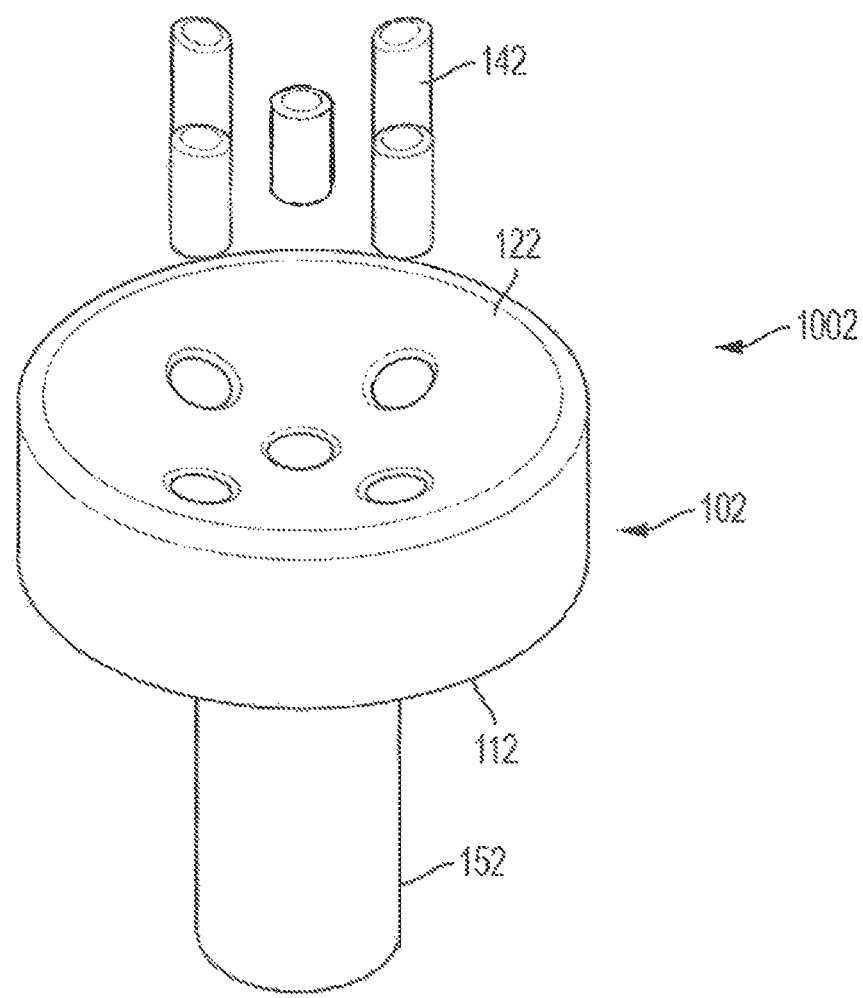
FIG. 12 shows an exploded perspective view of an apparatus in accordance with a third exemplary embodiment of the present invention.
Figure 13:
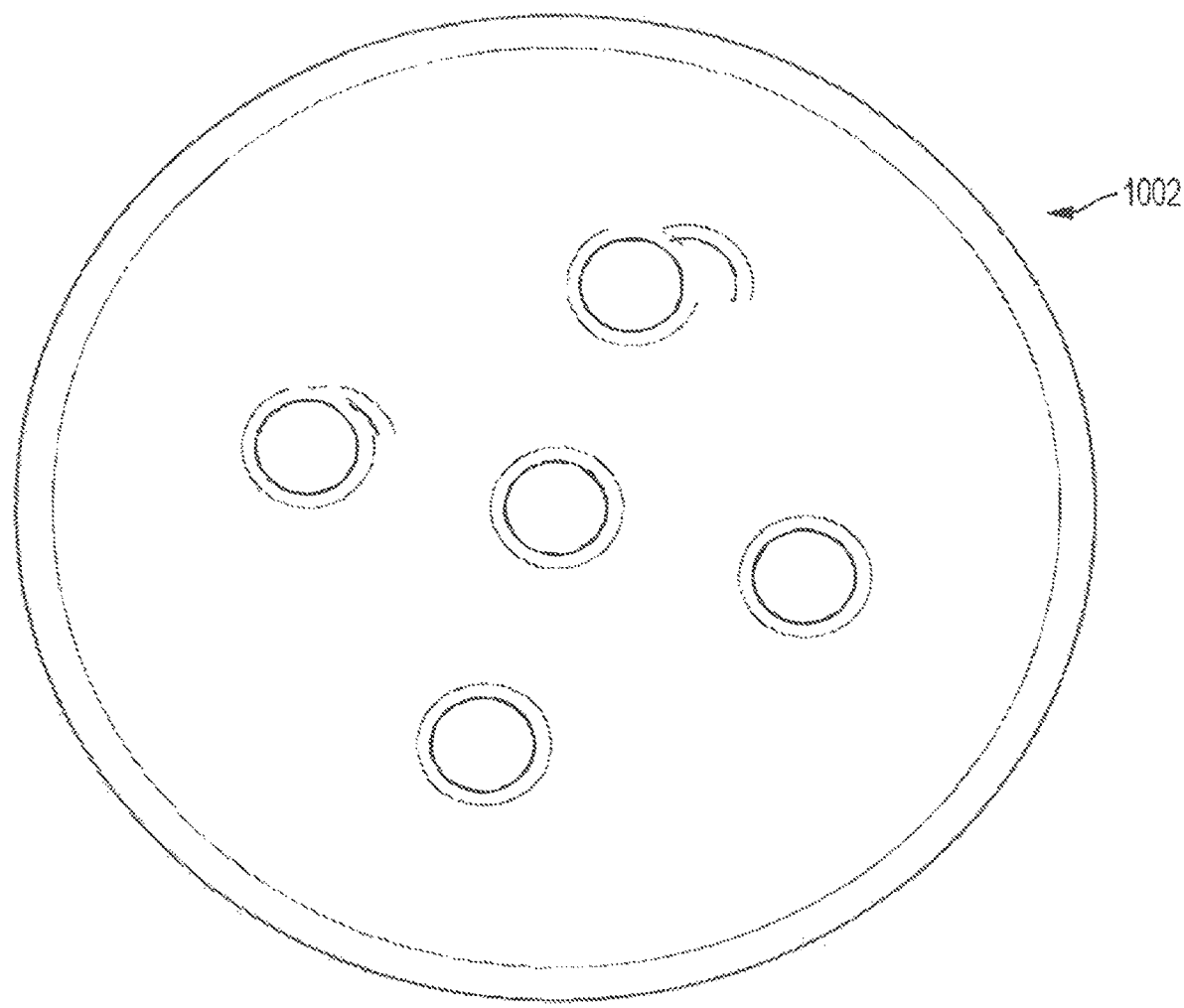
FIG. 13 shows a top view of an apparatus in accordance with a third exemplary embodiment of the present invention.
Figure 14:
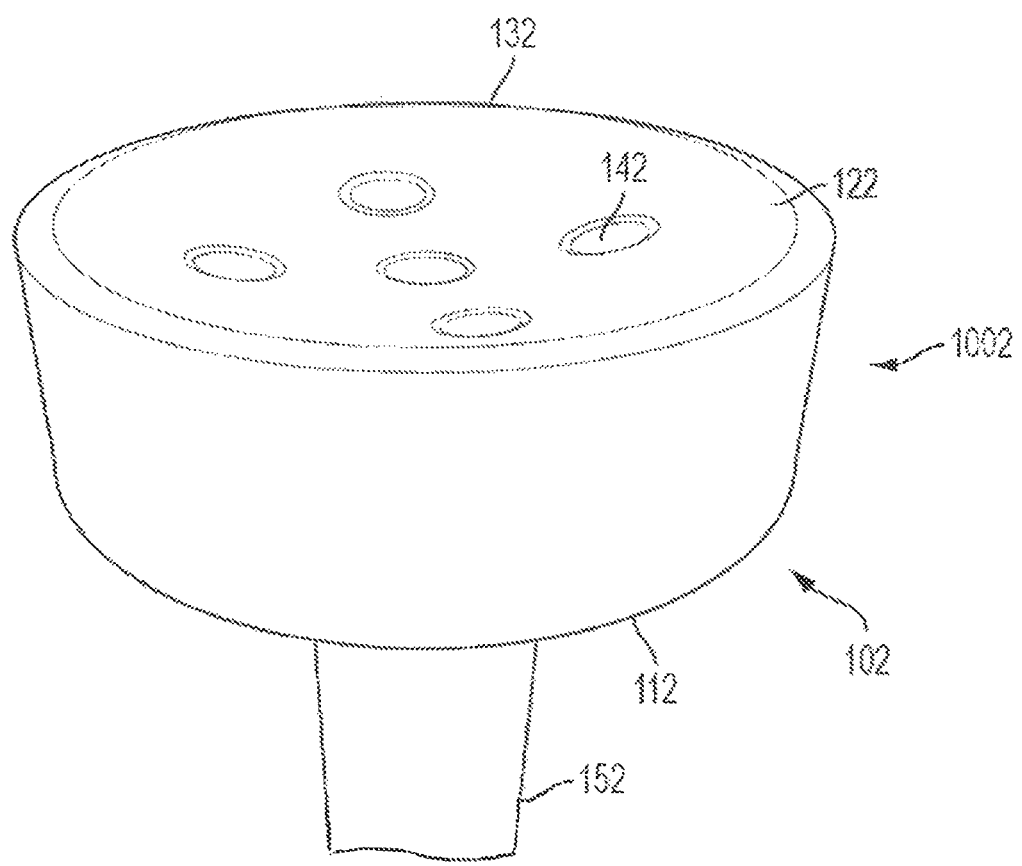
FIG. 14 shows a side perspective view of an apparatus in accordance with a third exemplary embodiment of the present invention.
Figure 15:
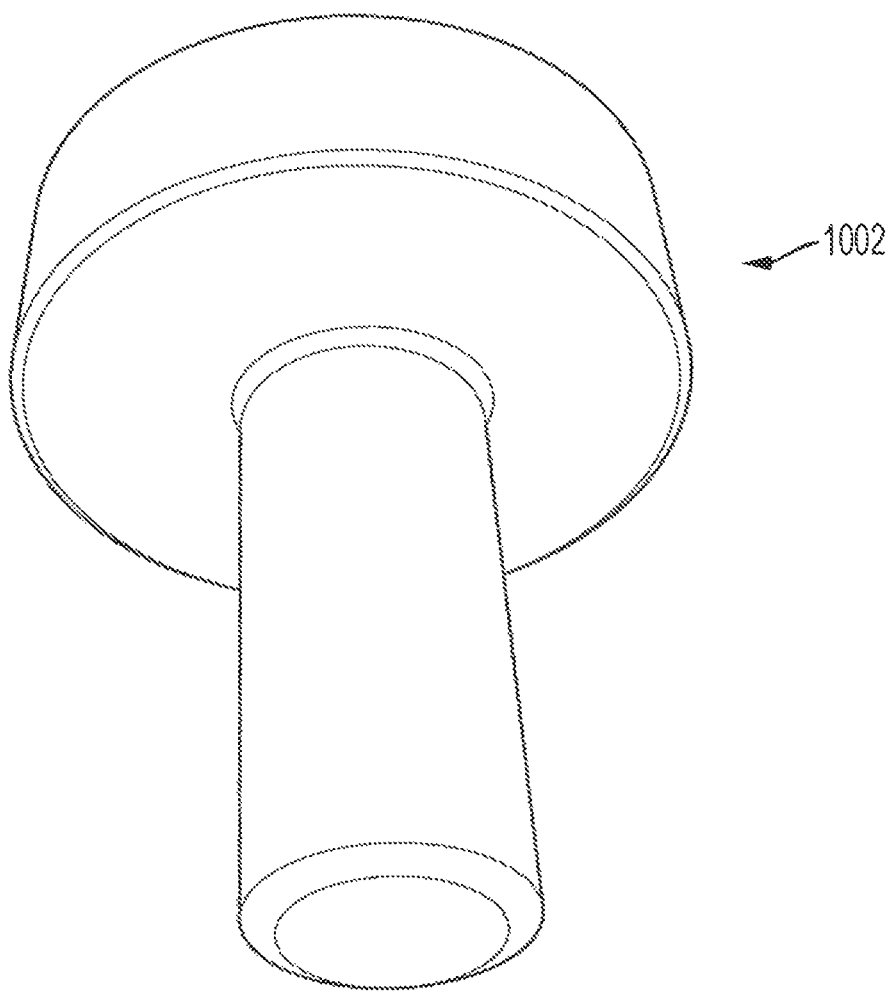
FIG. 15 shows a bottom perspective view of an apparatus in accordance with a third exemplary embodiment of the present invention.
Figure 16:
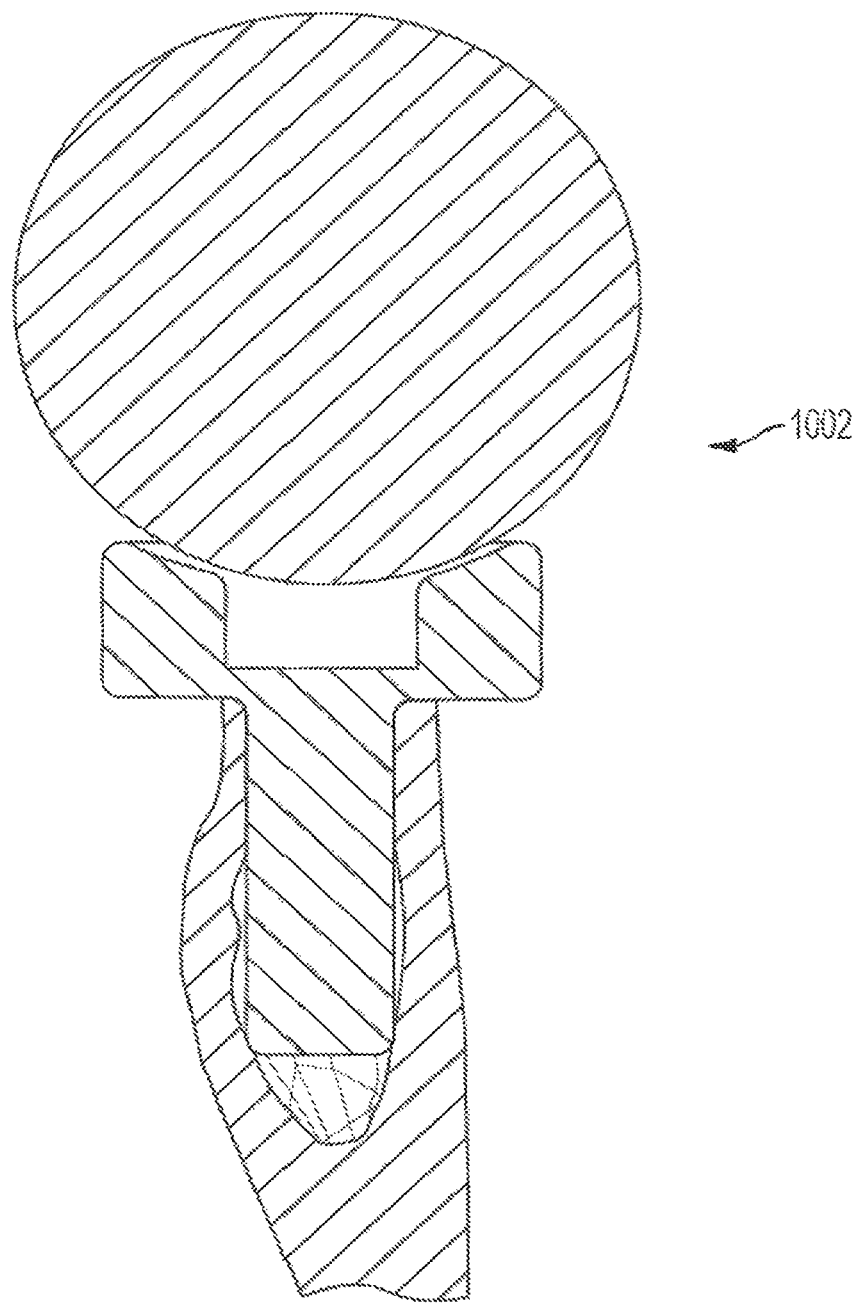
FIG. 16 shows a side view of an apparatus in accordance with a third exemplary embodiment of the present invention inserted into a radius bone.

Referring still to FIGS. 12-1.5, body 102 of apparatus 1002 has a generally cylindrical shape and a flat bottom surface 112. Body 102 further comprises a concave upper surface 122 disposed opposite said bottom surface 112.

Referring again to FIGS. 12-15, body 102 of apparatus 1002 further comprises a plurality of plugs 142. Plugs 142 preferably have rounded top surfaces and varying heights above upper surface 122 to maintain a generally concave topology. Each plug 142 comprises a second material distinct from the material of body 102 such as a biocompatible plastic polymer or thermoset polymer. Plugs 142 may comprise polyethylene, ultra-high molecular weight polyethylene, cross-linked polyethylene, or other non-metal materials as described above.

Referring still to FIGS. 12-15, body 102 of apparatus 1002 further comprises at least one stem 152. Stem 152 extends from bottom surface 110 of body 102 in a direction opposite top surface 122 of body 102. Stem 152 may comprise a smooth surface, a porous surface, or bone growth promoting materials. It is further contemplated that a plurality of stems 152 may be provided to attach body 102 to a human radius.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. A method of implanting a radial orthopedic implant apparatus, the method comprising the steps of:
    coupling an insert member to a generally cylindrical body by inserting the insert member into a centrally disposed bore of the body that is extends along a longitudinal axis through a concave upper surface of the body that has a bottom surface opposite the upper surface along the longitudinal axis, wherein the body includes at least one stem that extends from the bottom surface, and the body and insert member comprise respective first and second materials that are different from each other; and
    implanting the coupled insert member and the body into a medullary canal of a radial bone
    wherein the coupling step comprises inserting the insert member into the bore such that no portion of the insert member extends out with respect to the concave upper surface of the body in an upward direction that is defined from the bottom surface of the body toward the concave upper surface of the body along the longitudinal axis.

2. The method of claim 1, wherein the bottom surface is a flat bottom surface.

3. The method of claim 1, wherein after the coupling step, no portion of the insert member overlaps the concave upper surface of the body along a direction parallel to the longitudinal axis.

4. The method of claim 1, wherein said first material is a biocompatible metal.

5. The method of claim 4, wherein said biocompatible metal is selected from the group consisting of cobalt chrome, stainless steel, and titanium.

6. The method of claim 4, wherein said second material is a biocompatible plastic.

7. The method of claim 6, wherein said biocompatible plastic is selected from the group consisting of polyethylene, cross-linked polyethylene, hydrogel ceramic, PEEK, and ultra-high molecular weight polyethylene.

8. The method of claim 7, wherein said biocompatible metal is selected from the group consisting of cobalt chrome, stainless steel, and titanium.

9. The method of claim 1, wherein said stem is smooth.

10. The method of claim 1, wherein the insert member and the bore are cylindrical.

11. The method of claim 1, wherein the bore is a single bore and the insert member is a single insert member.

12. The method of claim 1, wherein the insert member is sized substantially equal to the bore in a plane that is oriented perpendicular to the longitudinal axis.

13. A method of implanting a radial orthopedic implant apparatus having an insert member, and a generally cylindrical body that includes at least one stem that extends from a bottom surface of the body, the method comprising the steps of:
    coupling the insert member to the body by inserting one of the body and the insert member into a bore of the other of the body and the insert member, wherein the body has a concave upper body surface disposed opposite the bottom surface of the body, and the insert member has a bottom insert member surface and an upper insert member surface disposed opposite the bottom insert member surface,
    wherein after the coupling step, the bottom insert member surface faces the body, and no portion of the upper insert member surface is disposed outward with respect to the upper body surface in an upward direction that is defined from the bottom surface of the body toward the upper body surface; and
    implanting the coupled insert member and the body into a medullary canal of a radial bone, wherein the body comprises a first material and the insert member comprises a second material that is different than the first material,
    wherein no portion of the insert member overlaps the concave upper body surface along a direction parallel to a longitudinal axis that extends centrally through the insert member from the bottom insert member surface to the upper insert member surface.

14. The method of claim 13, wherein no portion of the insert member overlaps the concave upper body surface along a direction parallel to the longitudinal axis.

15. The method of claim 13, wherein the insert member is sized substantially equal to the bore in a plane that is oriented perpendicular to the longitudinal axis.

16. The method of claim 13, wherein the body defines the bore, and the coupling step comprises the step of inserting the insert member into the bore of the body.

17. The method of claim 13, wherein the first material is a biocompatible metal.

18. The method of claim 17, wherein said second material is a biocompatible plastic.

19. The method of claim 13, wherein the insert member and the bore are cylindrical.

* * * * *